United States Patent [19]

Kawana et al.

[11] Patent Number: 4,956,149
[45] Date of Patent: Sep. 11, 1990

[54] BIOSENSOR DEVICE PROVIDED WITH AN AGITATOR

[75] Inventors: Yoshie Kawana; Narushi Ito, both of Tokyo, Japan

[73] Assignee: NEC Corporation, Japan

[21] Appl. No.: 213,076

[22] Filed: Jun. 29, 1988

[30] Foreign Application Priority Data

Jul. 2, 1987 [JP] Japan .................................. 62-166342

[51] Int. Cl.⁵ .............................................. G01N 27/00
[52] U.S. Cl. ................................... 422/68.1; 436/150; 366/127; 422/82.01
[58] Field of Search ................ 422/58, 68, 98; 366/117, 120, 127; 204/1 T, 403, 406, 415, 222; 73/61 R, 866.5; 435/15, 291; 436/95, 150; 310/328

[56] References Cited

U.S. PATENT DOCUMENTS

| | | | |
|---|---|---|---|
| 2,578,505 | 12/1951 | Carlin | 366/127 |
| 3,598,712 | 8/1971 | Petersen | 204/420 |
| 3,771,361 | 11/1973 | Reznick | 204/222 |
| 4,204,917 | 5/1980 | Yamamoto et al. | 422/98 |
| 4,216,671 | 8/1980 | Kurland | 73/61 R |
| 4,265,544 | 5/1981 | Banno et al. | 435/291 |
| 4,764,021 | 8/1988 | Eppes | 310/328 |
| 4,789,804 | 12/1988 | Karube et al. | 73/61 R |

FOREIGN PATENT DOCUMENTS 654299 12/1962 Canada ................................. 204/58

Primary Examiner—Robert J. Warden
Assistant Examiner—D. John Griffith, Jr.
Attorney, Agent, or Firm—Laff, Whitesel, Conte & Saret

[57] ABSTRACT

A biosensor includes an elastic substrate, a sensor tip, and a piezoelectric actuator. The sensor tip is mounted on one end of the substrate. The piezoelectric actuator is provided on the other end of the substrate.

2 Claims, 1 Drawing Sheet

BIOSENSOR DEVICE PROVIDED WITH AN AGITATOR

BACKGROUND OF THE INVENTION

The present invention relates to a biosensor device.

Recently, small ion sensors and semiconductor biosensor devices using them have been developed using a semiconductor manufacturing technique. A semiconductor biosensor device has a size of, e.g., about 0.6 mm×0.3 mm ×4 mm, and the sensing region of the probe is located within 1 mm from its distal end. Therefore, measurement can be performed even if a total amount of liquid to be measured is 30 μl or less.

Heretofore, a chemical substance in a solution was sensed by immersing a sensor of this type. The measured result was not reliable due to a poor reproducibility. If the amount of the solution including the substance to be sensed is small, the sensed output is not reliable at all.

SUMMARY OF THE INVENTION

It is an object of the present invention to provide a biosensor for measuring a small amount of solution with a high reproducibility.

According to the present invention, there is provided a biosensor comprising an elastic substrate, a sensor tip mounted on one end of the substrate, and a piezoelectric actuator provided on the other end of the substrate.

BRIEF DESCRIPTION OF THE DRAWINGS

The above and other objects and features of the invention will become more apparent from the following description taken in conjunction with the accompanying drawings; wherein.

DETAILED DESCRIPTION OF THE PREFERRED EMBODIMENT

A preferred embodiment of the present invention will be described in detail with reference to the accompanying drawings.

Figures 1A, 1B:
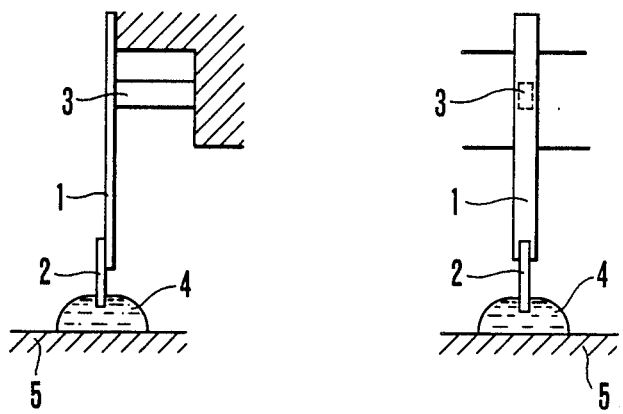
FIGS. 1(a) and 1(b) are side and front views, respectively, of a biosensor according to an embodiment of the present invention.
Figure 2:
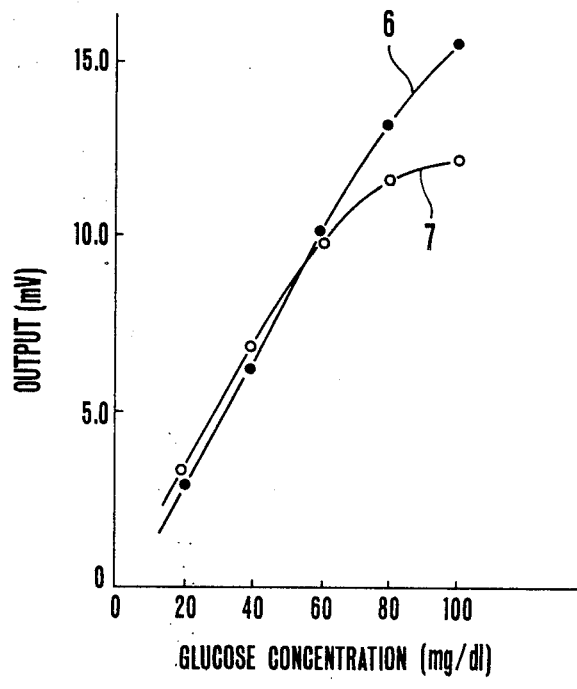
FIG. 2 is a graph showing the effect of the present invention.

Referring to FIGS. 1(a) and 1(b), a flexible ribbon connector 1 is made of an epoxy resin. A glucose sensor tip 2 is obtained by forming a glucose oxidase immobilized membrane in place of the gate electrode of a field effect transistor. One end of the sensor tip 2 is adhered to one end of the flexible ribbon connector 1. A laminated piezoelectric actuator 3 comprising, e.g., AE0505D08 available from NEC Corp. is mounted on the other end of the flexible ribbon connector 1. The piezoelectric actuator 3 is an element whose shape is changed in accordance with a voltage applied to it. When an arbitrary pulse is applied to the piezoelectric actuator 3, an arbitrary vibration can be supplied to the flexible ribbon 1. This vibration is amplified because of the elasticity of the flexible ribbon connector 1 and transmitted to the sensor tip 2 as a large displacement. The flexible ribbon connector 1, sensor tip 2 and the piezoelectric actuator 3 constitute a biosensor. The sensor tip may be mounted on the ribbon connector 1 in such a manner that it may be exchanged with a new one.

As shown in FIG. 1, when the sensor tip 2 is inserted in a droplet 4 of a solution to be measured and the piezoelectric actuator 3 is actuated, the concentration of the chemical substance in the solution can be measured by efficiently agitating the solution by the vibration transmitted from the flexible ribbon connector 1.

The operation of the biosensor will be described with reference to a case wherein the glucose concentration in a small amount of sample is measured. First, 24 μl of 20mN-2-Hydroxyethylpiperazine-N'-Z'-ethanesulfonic acid-NaOH buffer solution (pH 7.5, I=0.15) were dropped onto a fluororesin substrate 5 to form a droplet 4. The sensor tip 2 was inserted in the droplet 4. An electric pulse (pulse amplitude: 20 V, pulse width: 2.5 msec, frequency: 200 Hz) was applied to the piezoelectric actuator 3 to agitate the droplet 4. 6 μl of sample solution containing glucose were added to the droplet 4 while the droplet 4 was agitated. After the addition, the output was immediately increased to reach the steady state value within about 30 seconds.

FIG. 3 shows a calibration curve of a case wherein a biosensor according to the present invention is used and that of a case wherein the conventional apparatus is used. The conventional apparatus does not provide the agitator 3 and is used for sensing without agitating the droplet including substance to be sensed. Curve 6 indicates the result obtained with the biosensor according to the present invention, and curve 7 indicates the result obtained with the conventional biosensor. With the conventional biosensor, the output reaches a saturated value when the glucose concentration is about 80 mg/dl, whereas with the present invention, the output is substantially linearly increased up to about 100 mg/dl. The glucose sensor of this FET type is based on oxidation of glucose by oxygen contained in the solution. Therefore, it is assumed that when the glucose concentration is high, if agitation is insufficient, oxygen is not smoothly supplied, resulting in a decrease in output. It is apparent from this result that the agitation using the biosensor of the present invention is effective to obtain a reliable measurement with a high reproducibility.

As described above, with the biosensor device of the present invention, the concentration of a chemical substance in a small amount of sample can be measured with a high precision by using a small sensor provided with an agitator. The agitator can be made compact. When the agitator is built in a measuring device, the measuring device itself can be easily made compact. Furthermore, a measuring device can be provided at a low cost compared with a case wherein an agitator such as a motor is used.

What is claimed is:

1. A biosensor comprising:
    an elastic substrate having two ends;
    an electrode-type concentration sensor mounted on one end of said substrate; and
    a piezoelectric actuator on the other end of said substrate to operate as a vibrator,
    said substrate and said piezoelectric actuator being connected so that when said sensor is inserted in a droplet of a solution which is to be measured, a change in the shape of an element of said piezoelectric actuator is amplified by said substrate and transmitted to said sensor, and said sensor measures the concentration of a chemical substance while said sensor agitates the droplet.

2. A biosensor according to claim 1, wherein said sensor is mounted on said substrate in such a manner that said sensor may be exchanged with a new one.

* * * * *